United States Patent
Feiweier et al.

(10) Patent No.: US 9,557,248 B2
(45) Date of Patent: Jan. 31, 2017

(54) OPERATING METHOD FOR A COMPUTER TO DETERMINE AN OPTIMIZED MEASUREMENT SEQUENCE FOR A MEDICAL IMAGING SYSTEM

(71) Applicants: Thorsten Feiweier, Poxdorf (DE); Alto Stemmer, Erlangen (DE)

(72) Inventors: Thorsten Feiweier, Poxdorf (DE); Alto Stemmer, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 504 days.

(21) Appl. No.: 14/208,375

(22) Filed: Mar. 13, 2014

(65) Prior Publication Data

US 2014/0278195 A1  Sep. 18, 2014

(30) Foreign Application Priority Data

Mar. 13, 2013  (DE) .................. 10 2013 204 310

(51) Int. Cl.
*G01M 99/00* (2011.01)
*G06F 19/00* (2011.01)
(Continued)

(52) U.S. Cl.
CPC .......... *G01M 99/008* (2013.01); *G01R 33/543* (2013.01); *G01R 33/561* (2013.01);
(Continued)

(58) Field of Classification Search
CPC .. G01M 99/008; G01R 33/543; G01R 33/561; G06F 19/3406; G06F 19/321; A61B 8/54; A61B 6/586
See application file for complete search history.

(56) References Cited

U.S. PATENT DOCUMENTS 4,764,078 A * 8/1988 Neri .................... B25J 5/007
180/14.3
5,003,264 A * 3/1991 Koizumi .............. G01R 33/561
324/309
(Continued)

FOREIGN PATENT DOCUMENTS

CN  1626032 A  6/2005
JP  2005144075 A  6/2005
(Continued)

*Primary Examiner* — Ramesh Patel
(74) *Attorney, Agent, or Firm* — Schiff Hardin LLP (57) ABSTRACT

In a method for operating a medical imaging system and a medical imaging system operating according to such a method, a measurement sequence is divided into a number of partial sequences, with each of the partial sequences resulting in a loading of at least one of these system components when the measurement sequence is executed. The partial sequences are evaluated, in terms of their number and duration, using a computerized model in order to determine whether a load limit for the at least one of the system components is exceeded. If so, the number or duration of the partial sequences is modified, and a check using the computer model is again implemented. A number or respective duration of the partial sequences that results in the load limit not being exceeded is then used as a final output in order to operate the medical imaging system.

13 Claims, 7 Drawing Sheets

(51) Int. Cl.
  *G01R 33/54* (2006.01)
  *G01R 33/561* (2006.01)
  *A61B 6/00* (2006.01)
  *A61B 8/00* (2006.01)

(52) U.S. Cl.
  CPC .......... *G06F 19/3406* (2013.01); *A61B 6/586* (2013.01); *A61B 8/54* (2013.01); *G06F 19/321* (2013.01)

(56) References Cited

U.S. PATENT DOCUMENTS

| | | | | |
|---|---|---|---|---|
| 5,023,790 A * | 6/1991 | Luke, Jr. | ........ | G05B 19/41865 180/168 |
| 5,174,707 A * | 12/1992 | Suekane | ........ | A62C 3/00 29/711 |
| 5,832,051 A * | 11/1998 | Lutz | ........ | A61B 6/541 378/8 |
| 6,263,089 B1 * | 7/2001 | Otsuka | ........ | G06T 7/60 382/107 |
| 6,463,360 B1 * | 10/2002 | Terada | ........ | B25J 9/1679 318/568.12 |
| 8,482,282 B2 * | 7/2013 | Fautz | ........ | G01R 33/5659 324/307 |
| 8,633,690 B2 * | 1/2014 | Feiweier | ........ | G01R 33/54 324/307 |
| 8,712,714 B2 * | 4/2014 | Horger | ........ | A61B 5/055 702/104 |
| 8,816,688 B2 * | 8/2014 | Adachi | ........ | G01R 33/5659 324/318 |
| 8,884,619 B2 * | 11/2014 | Umeda | ........ | G01R 33/3607 324/307 |
| 8,994,372 B2 * | 3/2015 | Bitz | ........ | G01R 33/5612 324/307 |
| 9,198,598 B2 | 12/2015 | Kawamura et al. | | |
| 9,229,083 B2 * | 1/2016 | Fautz | ........ | G01R 33/5612 |
| 2002/0010519 A1 * | 1/2002 | Watanabe | ........ | G05B 15/02 700/83 |
| 2002/0157241 A1 * | 10/2002 | Yamamoto | ........ | B23P 21/004 29/705 |
| 2004/0263166 A1 * | 12/2004 | Kluge | ........ | G01R 33/583 324/309 |
| 2005/0189940 A1 * | 9/2005 | Feiweier | ........ | G01R 33/5612 324/307 |
| 2008/0024129 A1 * | 1/2008 | Heid | ........ | G01R 33/54 324/307 |
| 2008/0224699 A1 | 9/2008 | Hughes | | |
| 2009/0240379 A1 | 9/2009 | Feiweier | | |
| 2009/0274363 A1 | 11/2009 | Dai | | |
| 2010/0090694 A1 * | 4/2010 | Heid | ........ | A61B 5/055 324/309 |
| 2010/0111257 A1 | 5/2010 | Takekoshi | | |
| 2010/0217617 A1 | 8/2010 | Springorum et al. | | |
| 2011/0172515 A1 * | 7/2011 | Fautz | ........ | G01R 33/56 600/410 |
| 2013/0090776 A1 * | 4/2013 | Feiweier | ........ | A61B 6/586 700/295 |

FOREIGN PATENT DOCUMENTS

JP  2009034479 A  2/2009
WO  WO-95/34242 A1  12/1995

* cited by examiner

OPERATING METHOD FOR A COMPUTER TO DETERMINE AN OPTIMIZED MEASUREMENT SEQUENCE FOR A MEDICAL IMAGING SYSTEM

BACKGROUND OF THE INVENTION

Field of the Invention

The present invention concerns an operating method for a computer, that receives information about a measurement sequence to be implemented by a medical imaging system, wherein the measurement sequence includes a predetermined number of successive partial sequences, and wherein the execution of the partial sequences leads to a loading (stressing) of at least one component of the imaging medical technology system.

The present invention furthermore concerns a non-transitory computer-readable storage medium that includes machine code that can be executed directly by a computer, in order to cause the computer to be operated according to an operating method of the above type.

The present invention furthermore concerns a computer at which is stored such a computer program executable by the computer.

The present invention furthermore concerns a medical imaging system that has at least one component that is loaded by operation of the system with a measurement sequence composed of a predetermined number of partial sequences, and that has a control device designed as a computer of the type described above, or is connected with such a computer.

Description of the Prior Art

Methods, systems and computers of the above type are described in DE 10 2008 015 261 B4 and the corresponding US 2009/0 240 379 A1, for example.

In such known operating methods, using a model of the medical imaging system, a computer checks whether a resulting loading of the component of the medical imaging system remains below a load limit during the control of the medical imaging system with the measurement sequence. If yes, the computer retains the measurement sequence without modification. If no, the computer inserts a pause between two partial sequences that are in immediate succession.

The known operating method leads to good results if a partial sequence can be executed at any time, in principle. In some cases, however, the partial sequences must be executed in a number of measurement periods, with the measurement periods split into a measurement interval and a pause interval. In such cases, partial sequences can be executed only during the measurement intervals. In such cases, the known procedure does not always lead to optimal results. This is explained in detail in the following using an example.

It is assumed that a medical imaging system should be operated with a number of partial sequences, for example with 300 partial sequences. Each partial sequence requires 200 ms for its execution. An execution of the partial sequences one immediately after another (thus without pause between the individual partial sequences) leads to an impermissibly high loading of a component of the medical imaging system. By contrast, the loading remains within permissible bounds if a pause of 100 ms is respectively introduced between the partial sequences. Furthermore, it is assumed that the measurement sequence should be applied to a living examination subject, with applications of the partial sequences being executed only in phases in which a slight breathing-dependent movement occurs—for example only during breathing pauses or exhalation phases of the examination subject. A breathing period (=measurement period) amounts to 4 s, which is divided in equal parts into an exhalation or breath-hold phase (=measurement interval) and an inhalation or deep breathing phase (=pause interval).

In such a case, seven respective partial intervals can be assembled into a partial sequence group according to the procedure of the prior art. In this case, the duration of the partial sequence groups amounts to $$7 \times 200 \text{ ms} + 6 \times 100 \text{ ms} = 2000 \text{ ms} = 2 \text{ s}.$$

For 300 partial sequences in total, 300/7=43 partial sequence groups must thus be formed. The total duration for execution of the entire measurement sequence thus amounts to 43×4 s=172 s.

In the division of the measurement sequence into the individual partial sequence groups, in the prior art, no consideration is given to the fact that a pause interval (in the form of an inhalation or deep breathing phase) is inevitably present between each of the individual partial sequence groups. In some cases, it can be sufficient (or at least beneficial) to use the pause intervals in order to execute more partial sequences in the measurement intervals, and thus to reduce the number of measurement periods. This is also explained in detail in the following using an example.

Based on the above example, it is additionally assumed that the loading of the component of the medical imaging system remains within allowable bounds even if a pause of 10×100 ms=1000 ms=1 s is respectively introduced after ten respective partial sequences. In such a case, ten partial sequences can be combined into one partial sequence group. In this case, the duration of the partial sequence groups amounts to $$10 \times 200 \text{ ms} = 2000 \text{ ms} = 2 \text{ s}.$$

Nevertheless, the loading of the component of the medical imaging system remains within permissible bounds because a pause interval (=inhalation or deep breathing phase) respectively follows after the execution of the respective partial sequence group, which pause interval—with its duration of 2 s—exceeds the required minimum length of 1 s. For 300 partial sequences in total, it is no longer 43 partial sequence groups, but rather only 300/10=30 partial sequence groups that must be formed. The total duration for execution of the entire measurement sequence thus amounts to 30×4 s=120 s.

SUMMARY OF THE INVENTION

An object of the present invention is to achieve an optimal division of the partial sequences into the measurement intervals.

According to the invention, an operating method of the aforementioned type is designed so that the computer furthermore receives information about a measurement period and a division of the measurement period into a measurement interval and a pause interval.

The computer divides the partial sequences into a number of partial sequence groups and associates the partial sequence groups 1:1 with a corresponding number of measurement intervals.

After the division of the partial sequences into the partial sequence groups, using a model of the medical imaging system, the computer initially checks whether a resulting loading of the component of the imaging medical technology system during the control of said imaging medical technology system with the partial sequences of a respective individual partial sequence group remains below a load limit. If yes, the division that has been made is retained; and if no, the division of the partial sequences within the partial sequence groups is varied and/or the number of partial sequence groups is increased.

Using the model of the imaging medical technology system, the computer then checks whether the resulting loading of the component of the imaging medical technology system during the control of the medical imaging system with the measurement sequence in the implemented division of the partial sequences into the partial sequence groups remains below the load limit. If yes, the division that has been made is adopted as a final division, and an output group including at least one partial sequence group is formulated and emitted as an output from the computer. If no, the number of partial sequence groups and/or time intervals of the partial sequence groups from one another is increased.

The pause intervals as operating pauses thus can be considered in a simple manner by virtue of the operating method according to the invention, while the total duration of the measurement sequence is kept as short as possible.

The computer provides the entire measurement sequence as an output after the determination of the final division. Preferably, however, the computer provides the output groups as outputs in succession. In this case, the computer receives new information about the measurement period and the division of the measurement period into the measurement interval and the pause interval after the output of an output group.

Then the computer again divides the partial sequences that have not yet been output into a number of partial sequence groups, and associates the partial sequence groups 1:1 with a corresponding number of measurement intervals.

After the new division of the partial sequences into the partial sequence groups, the computer, using the model of the medical imaging system, initially checks whether a resulting loading of the component of the imaging medical technology system during the control of said imaging medical technology system with the partial sequences of a respective individual partial sequence group remains below a load limit. If yes, the newly conducted division is retained; and if no, the new division of the partial sequences within the partial sequence groups is varied and/or the number of partial sequence groups is increased.

Then, using the model of the imaging medical technology system, the computer checks whether the resulting loading of the component of the imaging medical technology system during the control of the medical imaging system with the measurement sequence in the newly conducted division of the partial sequences into the partial sequence groups remains below a load limit. If yes, an additional output group is emitted as an output. If no, the number of partial sequence groups and/or time intervals of the partial sequence groups from one another are increased.

In the event that the measurement period and its division changes during the emission of the output groups as an output, a tracking of the division that has been made can take place at any time.

In a further embodiment, after the new reception of the information about the measurement period and the division of the measurement period into the measurement interval and the pause interval, the computer checks whether the measurement interval and/or the pause interval have become shorter. If yes, the computer does not execute the tracking of the division that has been made. If no, the computer executes the tracking of the division that has been made.

In individual cases, it may occur that this procedure can lead to a (normally only slightly) suboptimal determination of the partial sequence groups. However, in contrast to this only then does a new determination of the division take place if there is a danger that the previous division can no longer be executed due to the variation of the measurement period and/or its division.

It is possible for the measurement period and the division of the measurement period into the measurement interval and the pause interval to be provided to the computer by a user. Alternatively, it is possible for the measurement period and the division of the measurement period into the measurement interval and the pause interval to be determined by the behavior of an examination subject who is to be exposed to the measurement sequence. For this purpose, the response of the examination subject (for example the subject's breathing movements or heartbeat) can be detected by a suitable measurement and be evaluated. In both cases, a safety factor can be taken into account in the determination of the measurement period and the division of the measurement period. This can make a re-determination of the division of the measurement sequence unnecessary during the control of the imaging medical technology system with the measurement sequence.

The computer can receive information about an initial load of the component of the imaging medical technology system, and can determine the resulting load under consideration of the initial load. The resulting load can be determined particularly accurately via this procedure.

It may be the case that, independent of pauses between the individual partial sequences, the execution of an individual partial sequence already leads to an overload of the component of the imaging medical technology system. In order to avoid such an overload, before the division of the partial sequences into the partial sequence groups, the computer (using the model of the imaging medical technology system) checks whether a resulting loading of the component of the medical imaging system during the control of the medical imaging system remains below a load limit during the control of said medical imaging system with the individual partial sequences. If yes, the computer retains the partial sequences. If no, the computer varies the partial sequences. The computer can reduce an amplitude with which the component of the medical imaging system is activated. Depending on the individual case, the reduction of the amplitude can be associated with a corresponding time extension of the partial sequence.

In many cases, it is possible for the computer to combine the partial sequences within the partial sequence groups into a single block. However, it normally leads to better results if the computer uniformly distributes the partial sequences within the partial sequence groups.

The computer preferably determines the resulting loading of the component of the medical imaging system using the particular partial sequence, among the partial sequences, that most strongly loads the component in question of the medical imaging system. Thus the resulting loading of the component of the medical imaging system must be determined only for a single partial sequence group. The computing cost can thereby be significantly reduced.

The computer can exclusively determine the division of the measurement sequence and provide the determined division as an output to a control device of the medical imaging system. The control device then controls the medical imaging system with the measurement sequence according to the final division.

The medical imaging system can be designed as any suitable imaging modality. In a preferred embodiment of the present invention, the medical imaging system is designed as a magnetic resonance system. In this case, the component of the medical imaging system that is evaluated as to its loading is any of a gradient power amplifier, a gradient coil, a radio-frequency power amplifier, or a radio-frequency transmission antenna.

The invention also encompasses a non-transitory, computer readable data storage medium encoded with programming instructions, such as machine code that, when the medium is loaded into a computer, cause the computer to operate according to the operating method according to the invention.

The invention also encompasses a computer programmed (configured) to execute the method according to the invention. As already mentioned, the computer can be designed as a control device for the medical imaging system.

The invention also encompasses a medical imaging system of the aforementioned type having a control device fashioned as a computer according to the invention, or connected with a computer according to the invention.

DESCRIPTION OF THE PREFERRED EMBODIMENTS

The present invention is explained in the following using the example of a magnetic resonance system. However, the procedures and embodiments according to the invention can also be realized by other medical imaging systems, for example C-arm x-ray systems, CT systems, ultrasound tomography systems, and the like.

Figure 1:
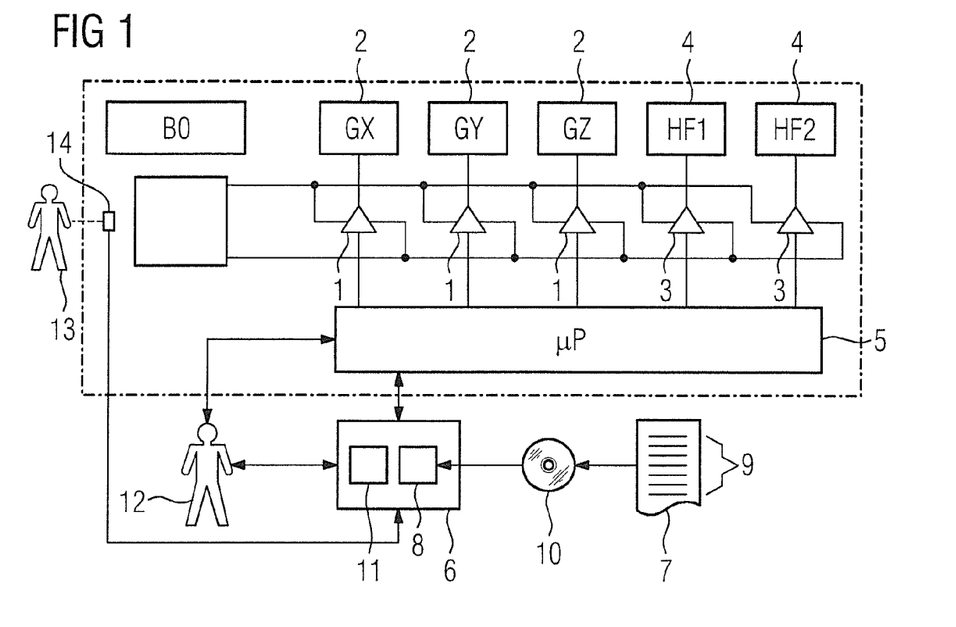
FIGS. 1 and 2 show respective embodiments of an imaging medical technology system in accordance with the invention.
Figure 2:
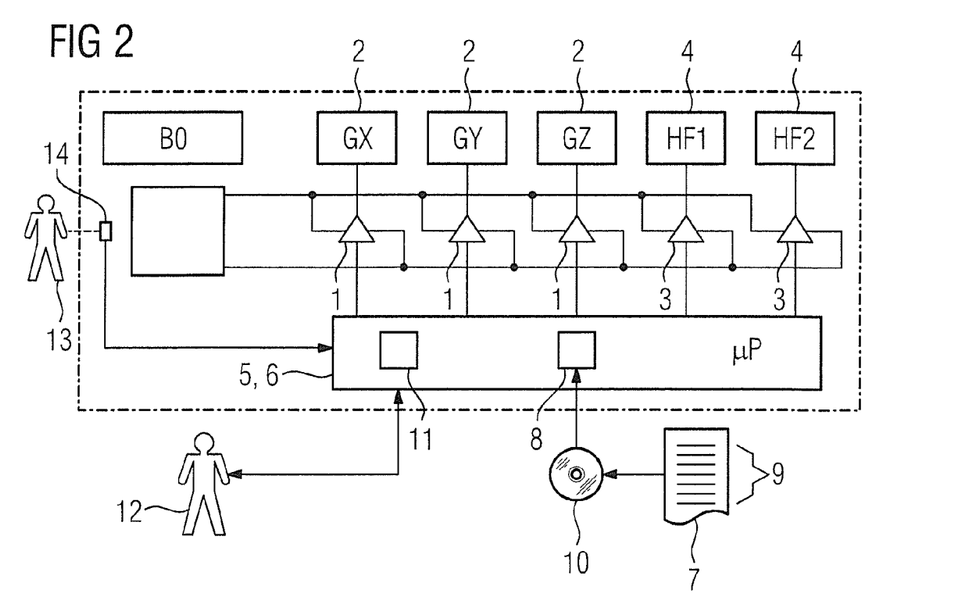

According to FIGS. 1 and 2, the medical imaging system has various components 1 through 4. For example, the components 1 through 4 are fashioned as a gradient power amplifiers 1, gradient coils 2, a radio-frequency power amplifier 3 and a radio-frequency transmission antennas 4.

Furthermore, the imaging medical technology system has a control device 5. The control device 5 is connected at least with the gradient power amplifiers 1 and the radio-frequency power amplifier 3 so that it can control these components 1, 3. The control device 5 is normally designed as a software-programmable control device. This is indicated in FIGS. 1 and 2 the symbol pP (for microprocessor) in the control device 5 in FIGS. 1 and 2.

It is possible for the control device 5 to be fashioned purely as a control device. This case is shown in FIG. 1. In this case, the control device 5 is connected with a computer 6. Alternatively, it is possible for the control device 5 to be fashioned as such a computer 6. This embodiment is depicted in FIG. 2.

Statements regarding the computer 6 and its operation (including the interaction with the control device 5) are made in the following in connection with FIG. 3 through 10.

In the event that the control device 5 is fashioned as a computer 6, the statements regarding the data exchange between the computer 6 and the control device 5 do not apply.

The computer 6 is software-programmable. In operation, it executes a computer program 7 that is stored in a memory device 8 of the computer 6. The computer program 7 includes machine code 9 that can be executed directly by the computer 6. The execution of the machine code 9 via the computer 6 has the effect that said computer 6 executes an operating method that is explained in detail in the following.

The computer program 7 can have been supplied to the computer 6 in various ways. For example, it is possible to supply the computer program 7 to the computer 6 via a connection to a computer network (for example the Internet or a LAN). Alternatively, it is possible to store the computer program 7 on a data medium 10 and to supply the computer program 7 to the computer 6 via the data medium 10. The data medium 10 can be designed as needed for this purpose. In FIGS. 1 and 2, a CD-ROM is shown. However, the data medium 10 could alternatively be fashioned as a USB memory stick or as a memory card, for example.

Figure 3:
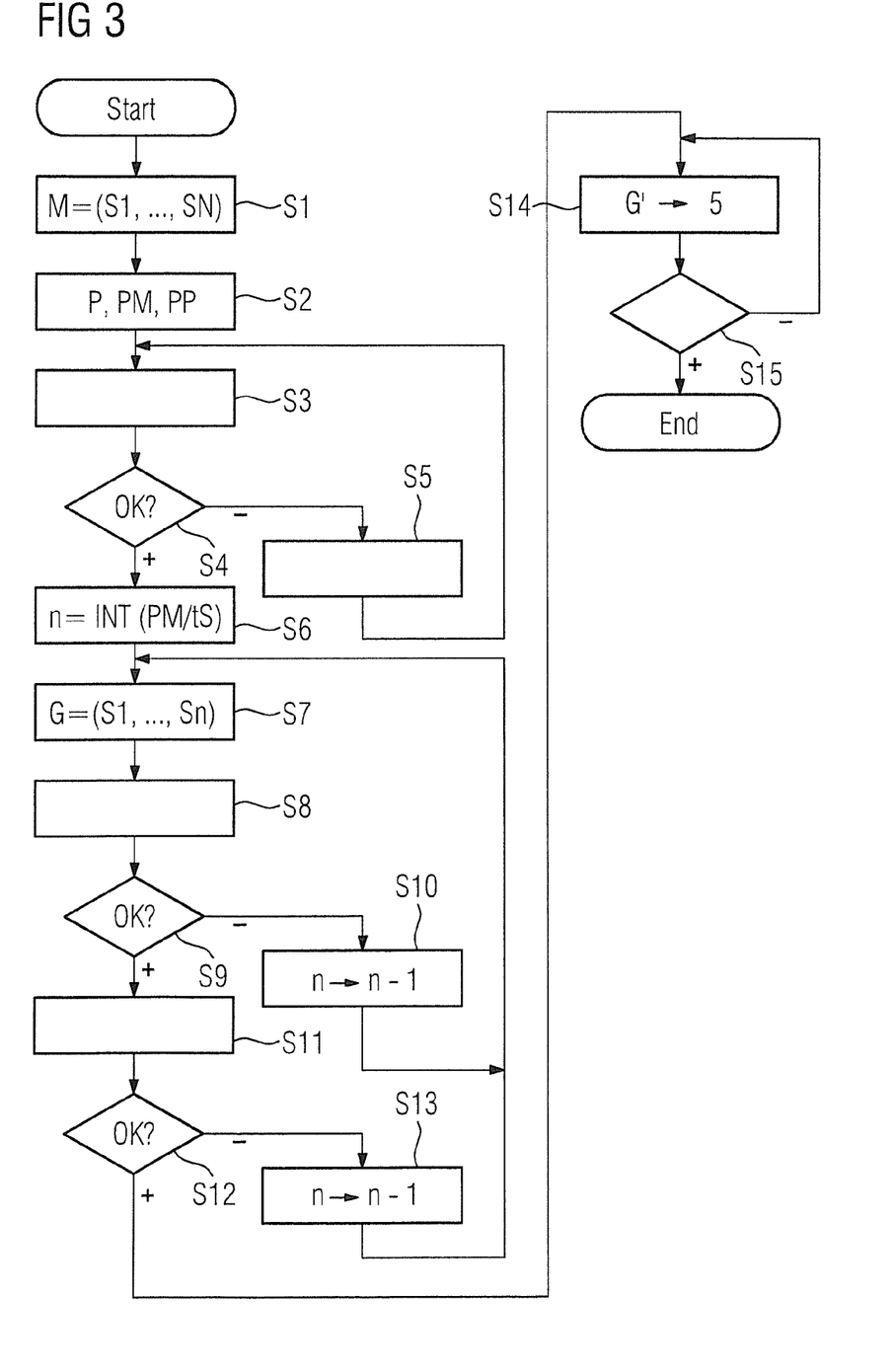
FIG. 3 shows a workflow diagram of an embodiment of the invention.

According to FIG. 3, in Step S1 the computer 6 receives information about a measurement sequence M. The measurement sequence M should be implemented by the imaging medical technology system. According to FIG. 4, the measurement sequence M consists of a predetermined number N of partial sequences S. The partial sequences S—and therefore as a result also the measurement sequence M—load the components 1 through 4 upon their execution. For example, given the execution of the partial sequences S, the gradient power amplifiers 1 and the gradient coils 2 are charged with gradient currents so that thermal loads occur in the gradient power amplifiers 1 and the gradient coils 2. The radio-frequency power amplifier 3 and the radio-frequency transmission antenna 4 can analogously be charged with radio-frequency currents so that thermal loads also occur in the radio-frequency power amplifiers 3 and the radio-frequency transmission antenna 4.

In Step S2, the computer 6 furthermore receives information about a measurement period P and a division of the measurement period P into a measurement interval PM and a pause interval PP. For example, the duration of the measurement period P and the relative or absolute proportion of the measurement interval PM can be provided to the computer 6. In such a case according to FIG. 5, the pause interval PP directly follows from the relation $$PM+PP=P.$$

Given the control of the imaging medical technology system with the partial sequences S of the measurement sequence M, partial sequences S may be executed only during the measurement intervals PM. No partial sequence S may be executed during the pause intervals PP.

Within the scope of the execution of the computer program 7, among other things the computer 6 implements a model 11 of the imaging medical technology system. By means of the model 11, the computer 6 can determine a respective loading of the components 1 through 4 that results during the controlling of the imaging medical technology system. This applies both to a controlling of the imaging medical technology system with an individual partial sequence S and to a controlling with a number of partial sequences S, wherein in the latter case the partial sequences S can alternatively follow one immediately after another or can be separated from one another in time. Such models 11 are known to person skilled in the art. The model 11 as such is thus assumed to be known within the scope of the present invention.

According to FIG. 3, using the model lithe computer 6 initially determines in Step S3 a loading of the components 1 through 4 that results given execution of the individual partial sequences S (thus respectively considered independently). In Step S4, the computer 6 checks (possibly individually for each component 1 through 4) whether the load determined in Step S3 remains below a load limit. If the load limit is exceeded, the computer 6 transitions to a Step S5. In Step S5, the computer 6 varies the partial sequences S. For example, it can reduce an amplitude. It can additionally extend the duration of the partial sequences S if necessary. The computer 6 then returns to Step S3. If the check in Step S4 turns out to be positive (thus if the load limit is thus not exceeded), the computer 6 retains the partial sequences S. In this case, it transitions from Step S4 to Step S6.

It is possible that the partial sequences S are equivalent in relation to the loading of the components of the components 1 through 4 in imaging medical technology systems. In this case, it is sufficient to implement Steps S3 through S5 only for a single partial sequence S. In the event that the partial sequences S load the components 1 through 4 to different degrees, it is possible that the computer 6 determines the respective resulting loading of the components 1 through 4 individually for the respective partial sequence S. However, the computer 6 advantageously determines the resulting load only for that partial sequence S which most strongly loads the components 1 through 4. Under the circumstances, this can in fact respectively be a different partial sequence S depending on components 1 through 4. Nevertheless, the cost is significantly reduced since Steps S3 through S5 must be implemented only for a few partial sequences S, not for all partial sequences S.

It is possible that which sequence among the partial sequences S most strongly loads the components 1 through 4 is known in advance to the computer 6. Alternatively, it is possible for the computer 6 to itself determine that partial sequence S (or the corresponding partial sequences S in the case of multiple components 1 through 4).

Furthermore, it is possible for the partial sequences S to already have been determined in advance, such that components 1 through 4 are not unnecessarily loaded by the execution of a single partial sequence S. In this case, Steps S3 through S5 can be omitted.

Figure 4:
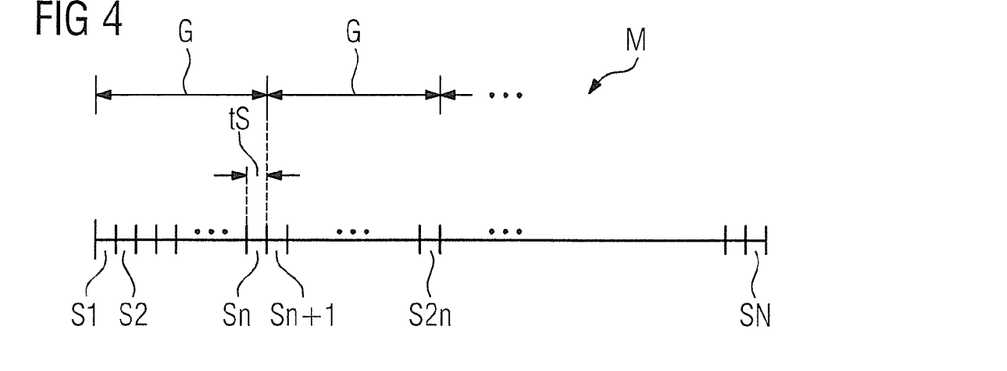
FIG. 4 shows a measurement sequence.
Figure 5:
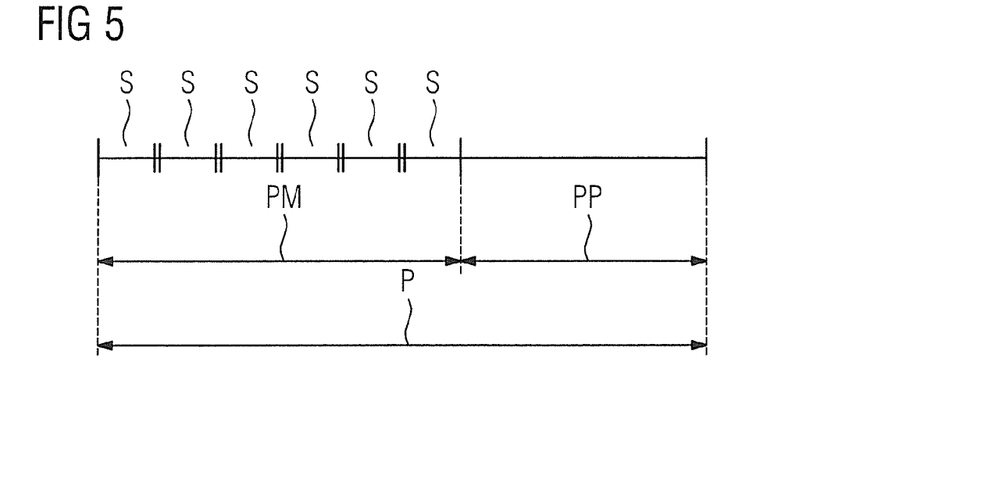
FIG. 5 shows a measurement period.
Figure 6:
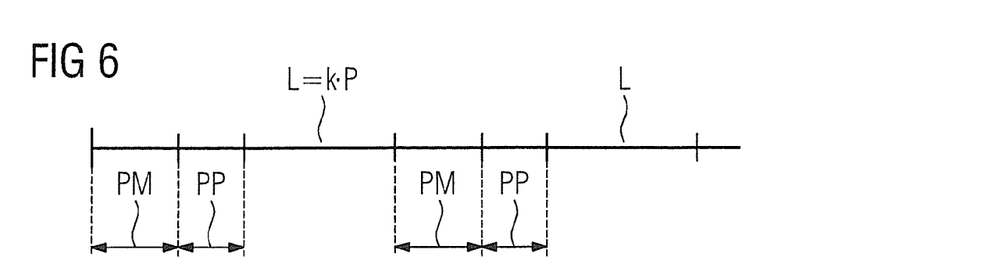
FIG. 6 shows multiple measurement periods.

In Steps S6 and S7, the computer 6 divides the partial sequences S into a number of partial sequence groups G (see FIG. 4). In particular, the computer 6 initially determines a number n within the scope of Step S6. The number n corresponds to a theoretical maximum possible number of partial sequences S per partial sequence group G. The number n results via the relation $$n=\text{INT}(PM/tS),$$

wherein tS is the duration of an individual partial sequence S. The actual division of the partial sequences S into the partial sequence groups G takes place in Step S7. Furthermore, within the scope of Step S7 the computer 6 associates the partial sequence groups G 1:1 with a corresponding number of measurement intervals PM. Each partial sequence group G is thus associated with a single measurement interval PM. Conversely, a partial sequence group G is associated with each measurement interval PM.

It is possible that, within the scope of Step S7, the computer 6 groups the partial sequences S within the partial sequence groups G as a contiguous block in which the partial sequences S are executed in immediate succession, without time interval. However, the computer 6 preferably distributes the partial sequences S uniformly within the partial sequence groups G. The first partial sequence S of a defined partial sequence group G thus advantageously begins with the beginning of the corresponding measurement interval PM, and the last partial sequence S of a defined partial sequence group G ends with the end of the corresponding measurement interval PM.

In Step S8, the computer 6 determines a loading of the components 1 through 4 that results given execution of the partial sequences S of a respective individual partial sequence group G. In Step S9, the computer 6 checks (possibly individually for each component 1 through 4) whether the load determined in Step S8 remains below the load limit. If the load limit is exceeded, the computer 6 transitions to Step S10. Under the circumstances, in Step S10 the computer 6 can vary the division of the partial sequences S within the partial sequence groups G. Such a variation can in particular be reasonable when the computer 6 groups the partial sequences S into a contiguous block within the partial sequence groups G. In each case, however, it is possible for the computer 6 to reduce the number n of partial sequences S per partial sequence group G. The computer 6 then returns to Step S7. Within the scope of Step S7, the number of partial sequence groups G thereby increases. In contrast to this, if the check in Step S9 turns out to be positive (thus if the load limit is not exceeded), the computer 6 retains the division that is made. In this case, it transitions from Step S9 to Step S11.

In the event that the partial sequences S are equivalent with regard to the loading of the components 1 through 4 of the imaging medical technology system, it is sufficient to implement Steps S8 through S10 only for a single partial sequence group G. In the event that the partial sequences load the components 1 through 4 to different degrees, it is possible that the computer 6 determines the respective resulting loading of the components 1 through 4 individually for the respective partial sequence group G. However, the computer 6 advantageously determines the resulting loading under the assumption that the partial sequences S of the partial sequence groups G correspond to that partial sequence S which most strongly loads the components 1 through 4. Under the circumstances, this may be a different partial sequence S, depending on components 1 through 4. Nevertheless, the cost is reduced significantly since Steps S8 through S10 must be implemented only for a few partial sequence groups G, not for all partial sequence groups G.

In Step S11, the computer 6 determines a loading of the components 1 through 4 that results given execution of the partial sequences S of all partial sequence groups G. The computer 6 thus determines a loading of the components 1 through 4 that results given execution of the entire measurement sequence M in the division that has been made. In Step S12, the computer 6 checks (if necessary, individually for each component 1 through 4) whether the load determined in Step S11 remains below the load limit. If the load limit is exceeded, the computer 6 transitions to Step S13.

In Step S13, the computer 6 can reduce the number n of partial sequences S per partial sequence group G. The reduction of the number n of partial sequences S per partial sequence group G corresponds (as before) to an increase of the number of partial sequence groups G. In this case, the computer 6 transitions from Step S13 back to Step S7. Alternatively or additionally, the computer 6 can increase time intervals of the partial sequence groups G from one another. In particular, the computer 6 can insert empty periods L between measurement periods P according to FIG. 6. The empty periods L have a whole-number multiple of the length of the measurement periods P. However, no partial sequences S are executed during the empty periods L. The number of empty periods L can be defined as needed. It is possible that an empty period L is always inserted between each two measurement periods P. Alternatively, only a few empty periods L can be inserted. If the computer 6 maintains the number n of partial sequences S per partial sequence group G, the computer 6 can likewise return back to Step S7. In this case, however, the computer 6 advantageously goes back to Step S11.

If the check in Step S12 turns out to be positive (thus the load limit is not exceeded), the computer 6 accepts the division that has been made as a final division. In this case, it transitions from Step S12 to Step S14. In Step S14, the computer 6 emits an output group G', as an output. The emitted output group G' includes at least one partial sequence group G. Alternatively, it can include multiple partial sequence groups G. It can even correspond to the entire measurement sequence M (according to the final division).

In the event that the emitted output group G' corresponds to the entire measurement sequence M, the procedure from FIG. 3 is ended. Otherwise, in Step S15 the computer 6 checks whether it has already completely emitted the measurement sequence M. If this is not the case, the computer 6 transitions back to Step S14, in which it outputs the next output group G'.

The output is normally provided to the control device 5. Alternatively, in individual cases it can be supplied to another device. In the event that the computer 6 is identical to the control device 5 (see FIG. 2), the computer 6 controls the imaging medical technology system with the measurement sequence M according to the final division.

The specification of the measurement period P and the division of the measurement period P into the measurement interval PM and the pause interval PP can take place in different ways. In particular, according to FIGS. 1 and 2 (for example) it is possible for a user 12 of the computer 6 to provide the corresponding values to the computer 6. Alternatively, according to FIGS. 1 and 2 it is possible for the measurement period P and the division of the measurement period P into the measurement interval PM and the pause interval PP to be determined by the behavior of an examination subject 13 who is to be exposed to the measurement sequence M. In this case, appropriate sensors 14 are present by means of which the relevant signal or the relevant signals are detected and supplied (directly or indirectly) to the computer 6. For example, the heartbeat of the examination subject 13 can be determined, and from this the cited values P, PM and PP can be derived. The respiration rhythm of the examination subject 13 can analogously also be detected and evaluated in this sense.

Figure 7:
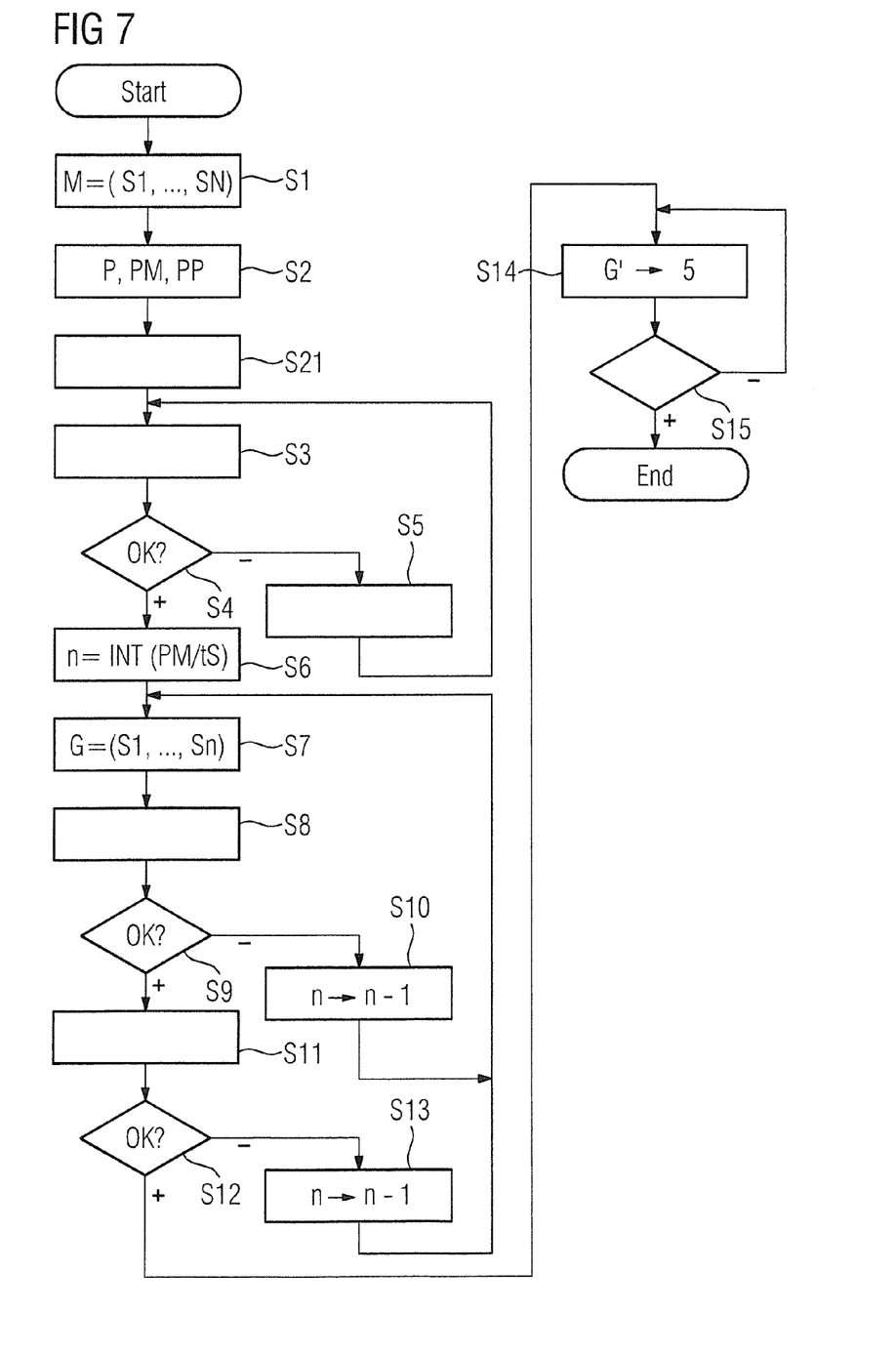
FIGS. 7 through 10 respectively show workflow diagrams of further embodiments of the invention.

FIG. 7 shows a modification of the procedure from FIG. 3. According to FIG. 7, a Step S21 is arranged before Step S3. According to FIG. 7, Step S21 is arranged immediately before Step S3. However, this is secondary. In Step S21, the computer 6 receives information about an initial load of the components 1 through 4.

Furthermore, Steps S3, S8 and S11 are slightly modified in the event of the presence of Step S21. In particular, the cited steps are modified to the effect that the computer 6 determines the respective resulting load under consideration of the initial load.

Figure 8:
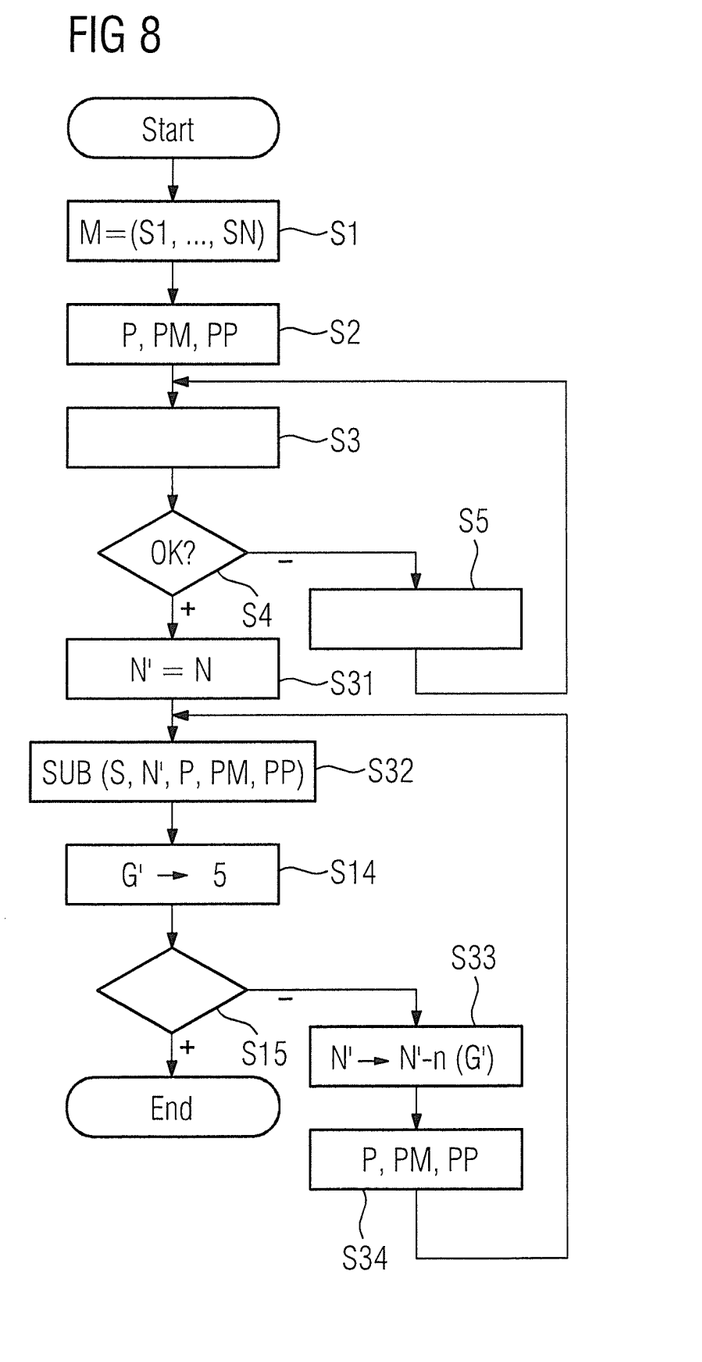

FIG. 8 shows a further modification of the method from FIG. 3. This modification can be combined with the modification according to FIG. 7. However, it can be realized independently of this.

According to FIG. 8, Steps S31 and S32 are present instead of Steps S6 through S13. In Step S31, the computer 6 sets a number N' to a value of N, i.e. the number of partial sequence groups S of the measurement sequence M. The computer 6 then calls a sub-program in Step S32. In the sub-program call, the computer 6 transfers to the sub-program a partial sequence S (including its description), the number N', the measurement period P, and the division of the measurement period P into the measurement interval PM and the pause interval PP. The associated sub-program is shown in FIG. 9, and includes Steps S6 through S13.

Furthermore, Steps S33 and S34 are arranged after the No-branch of Step S15. In Step S33, the computer 6 reduces the number N' by the number of partial sequences S that it has output in the immediately preceding execution of Step S14. The number N' thus corresponds to the number of partial sequences that are yet to be output. Furthermore, in Step S34 (analogous to Step S2) the computer 6 receives information about the measurement period P and the division of the measurement period P into the measurement interval PM and the pause interval PP. Furthermore, after the execution of Step S34 the computer 6 does not go back to Step S14, but rather to Step S32.

Figure 9:
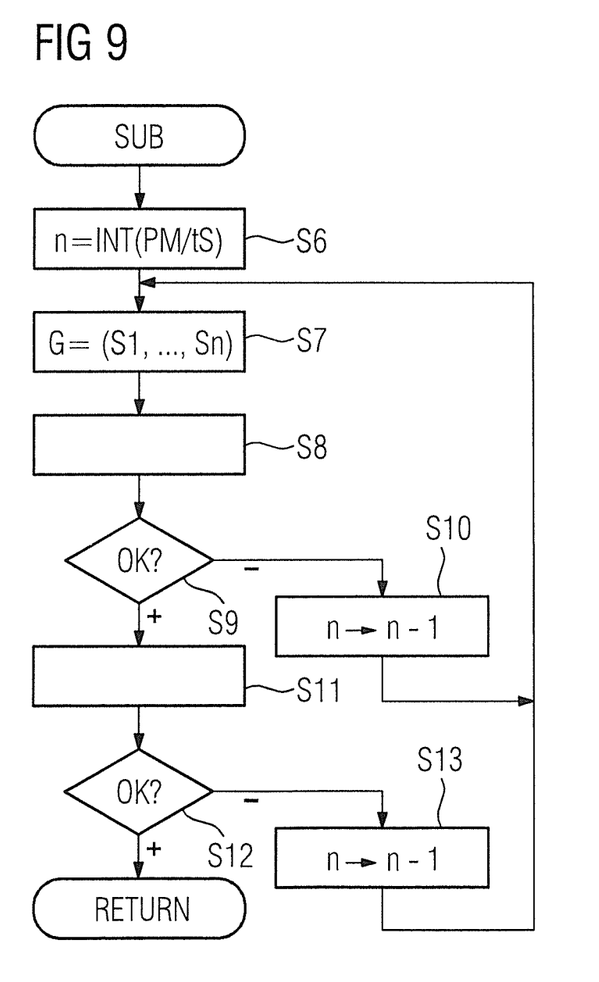

Within the scope of the procedure of FIGS. 8 and 9, the computer 6 thus successively outputs the output groups G', wherein after the output of an output group G' it newly receives the information about the measurement period P and its division. The computer 6 then executes the operating method according to the invention again relative to the partial sequences S that have not yet been output. A dynamic adaptation of the division of the partial sequences S into the partial sequence groups G, and their association with the measurement intervals PM, thus takes place. The operating method according to the invention is thereby applicable even when dynamic modifications of the measurement period P or its division can occur.

Figure 10:
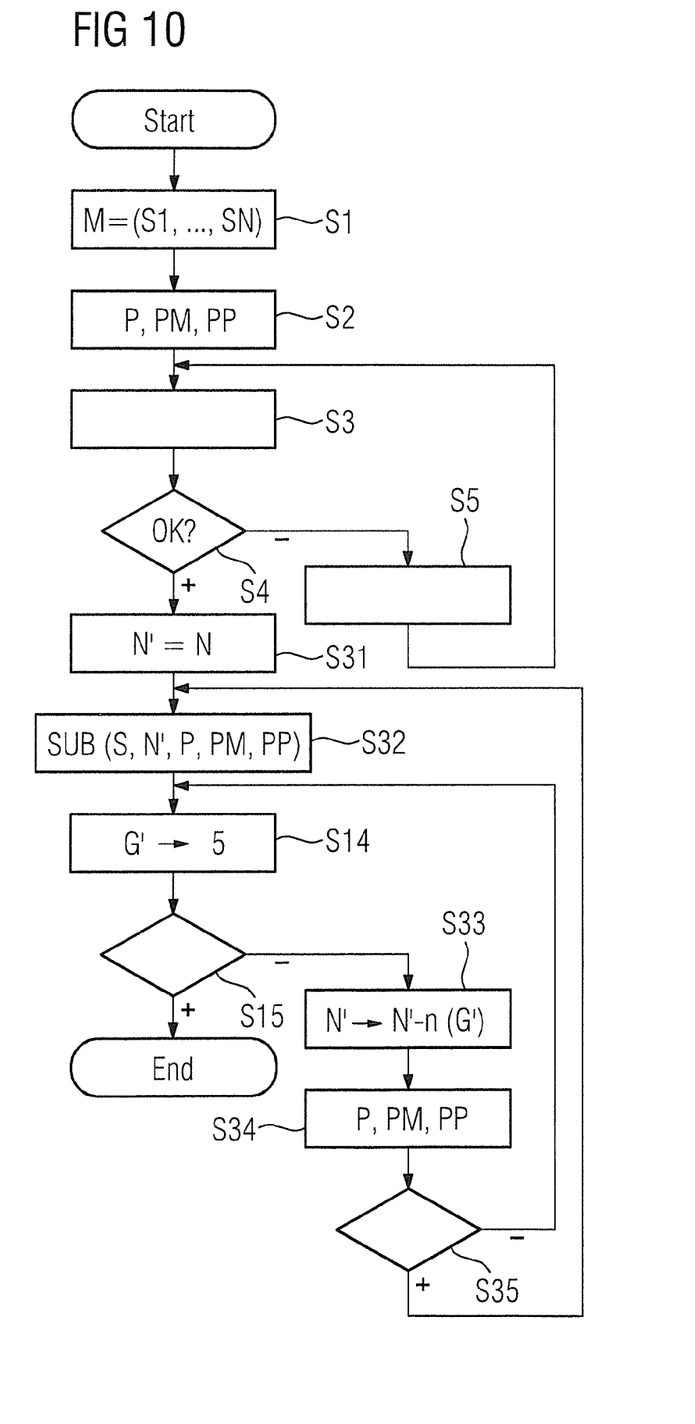

It is possible to modify the procedure from FIG. 8 according to FIG. 10. According to FIG. 10, a Step S35 is arranged after Step S34. In Step S35, the examiner 6 checks whether the measurement interval PM and/or the pause interval PP have become short (relative to the previously valid values). If this is the case, the computer 6 goes back to Step S32. Otherwise, the computer 6 goes back to Step S14. This results in the computer 6 conducting the new division of the partial sequences S that have not yet been output at this point in time if and only if the measurement interval PM and/or the pause interval PP have become shorter, and the danger thereby exists that the previously determined division of the measurement sequence M can no longer or may no longer be executed.

The procedures according to the invention lead in a simple manner to a time-optimized division of the partial sequences S to be output into the provided measurement intervals PM. Time savings of up to 50% can be achieved.

Although modifications and changes may be suggested by those skilled in the art, it is the intention of the inventors to embody within the patent warranted hereon all changes and modifications as reasonably and properly come within the scope of their contribution to the art.

We claim as our invention:

1. A method for operating a computer to generate an operating sequence, with which said computer operates a medical imaging system, said medical imaging system comprising a plurality of components, said method comprising:

in said computer, receiving an electronic designation of a measurement sequence to be executed by said medical imaging system, said measurement sequence comprising a predetermined number of successive partial sequences that each, when executed by said medical imaging system, cause a loading of at least one of said components;

in said computer, also receiving an electronic designation of a measurement period and a division of said measurement period into a measurement interval and a pause interval;

in said computer, automatically dividing said partial sequences into a plurality of partial sequence groups, and designating an initial association of said plurality of partial sequence groups to an equal plurality of said measurement intervals, with a one-to-one relation of said plurality of partial sequence groups to said plurality of measurement intervals;

in said computer, operating a computerized model of said medical imaging system to initially check whether a loading of at least one of said components with the partial sequences of a respective individual partial sequence group is below a load limit and, if so, retaining said divisions of said partial sequences of said respective individual partial sequence group and, if not, modifying said division of said partial sequences within said respective individual partial sequence group, and/or increasing said plurality of partial sequence groups, thereby obtaining at least one of a modified grouping and a modified number of groups;

in said computer, operating said computerized model of said medical imaging system to check whether said modified grouping or said modified number of groups results in a loading of said at least one component that is below said load limit and, if so, adopting said modified grouping or said modified number of groups as said final division and, if not, again modifying said at least one of said grouping and said number of groups until a modified grouping or a modified number of groups, when said operating said computerized model, results in a loading of said at least one component that is below said load limit, as said final grouping or final number of groups; and emitting a designation of said plurality of partial sequences as a final output, that conforms to said final grouping or said final number of groups, in electronic form from an output of said computer in a format configured to operate said medical imaging system.

2. A method as claimed in claim 1, comprising:

in said computer, receiving another, different electronic designation of said measurement period and said division of said measurement period into said measurement interval and said pause interval;

in said computer, automatically checking (a) whether the measurement interval in said another, different electronic designation of said measurement period is shorter than the measurement interval in said electronic designation of said measurement period and (b) whether said pause interval in said another, further electronic designation of said measurement period is shorter than the pause interval in said electronic designation of said measurement period;

if nether (a) nor (b) occurs, maintaining said final grouping or final number of groups; and if either (a) or (b) occurs, executing an additional determination in said computer of said final grouping or said final number of groups.

3. A method as claimed in claim 2 comprising, in said additional determination of said final grouping or said final number of groups in said computer;

in said computer, automatically dividing any of said partial sequences that are not included in said final output, as partial sequence groups subject to said additional determination, into a plurality of partial sequence groups subject to said additional determination, and designating an initial association of said plurality of partial sequence groups subject to said additional determination to an equal plurality of said measurement intervals, with a one-to-one relation of said plurality of partial sequence groups to said plurality of measurement intervals;

in said computer, operating said computerized model of said medical imaging system to initially check whether a loading of at least one of said components with the partial sequences subject to said additional determination of a respective individual partial sequence group subject to said additional determination is below a load limit and, if so, retaining said divisions of said partial sequences subject to said additional determination of said respective individual partial sequence subject to said additional determination group and, if not, modifying said division of said partial sequences subject to said additional determination within said respective individual partial sequence group subject to said additional determination, and/or increasing said plurality of partial sequence groups subject to said additional determination, thereby obtaining at least one of an additional modified grouping and an additional modified number of groups;

in said computer, operating said computerized model of said medical imaging system to check whether said additional modified grouping or said additional modified number of groups results in a loading of said at least one component that is below said load limit and, if so, adopting said additional modified grouping or said additional modified number of groups as said final division and, if not, again modifying said at least one of said grouping and said number of groups until a modified grouping or a modified number of groups, when said operating said computerized model, results in a loading of said at least one component that is below said load limit, as said final grouping or final number of groups; and emitting a further designation of said plurality of partial sequences subject to said additional determination, that conforms to said final grouping or said final number of groups resulting from said additional determination, in electronic form from an output of said computer in a format configured to operate said medical imaging system.

4. A method as claimed in claim 1 wherein said measurement sequence is to be executed by said medical imaging system on an examination subject, and setting said measurement period and said division of said measurement period into said measurement interval and said pause interval dependent on behavior of said examination subject.

5. A method as claimed in claim 1 comprising receiving said measurement period and said division of said measurement period into said measurement interval and said pause interval into said computer via an input made by a user via a user interface of said computer.

6. A method as claimed in claim 1 comprising:
in said computer, receiving an electronic designation of an initial load of said at least one of said components, and determining said resulting load of said at least one of said components dependent on said initial load.

7. A method as claimed in claim 1 comprising:
before dividing said partial sequences into said partial sequence groups by operating said computerized model of said medical imaging system, checking in said computer, whether a resulting loading of said least one components by execution of individual partial sequences, without division in two groups, is below said load limit and, if so, retaining said partial sequences with no grouping thereof, as said final output.

8. A method as claimed in claim 1 comprising uniformly modifying said partial sequences within said partial sequence groups.

9. A method as claimed in claim 1 comprising determining said resulting loading of said at least one of said components using a partial sequence, among said plurality of partial sequences, that most strongly loads said at least one component.

10. A method as claimed in claim 1 wherein said medical imaging system is a magnetic resonance system and wherein said components comprise at least one gradient power amplifier, at least one gradient coil connected to said at least one gradient power amplifier, a radio-frequency power amplifier, and a radio-frequency transmission antenna connected to said radio-frequency power amplifier.

11. A non-transitory, computer-readable data storage medium encoded with programming instructions, said storage medium being loaded into an operating computer for operating a medical imaging system comprising a plurality of components, said programming instructions causing said operating computer to:
receive an electronic designation of a measurement sequence to be executed by said medical imaging system, said measurement sequence comprising a predetermined number of successive partial sequences that each, when executed by said medical imaging system, cause a loading of at least one of said components;
also receive an electronic designation of a measurement period and a division of said measurement period into a measurement interval and a pause interval;
automatically divide said partial sequences into a plurality of partial sequence groups, and designate an initial association of said plurality of partial sequence groups to an equal plurality of said measurement intervals, with a one-to-one relation of said plurality of partial sequence groups to said plurality of measurement intervals;
operate a computerized model of said medical imaging system to initially check whether a loading of at least one of said components with the partial sequences of a respective individual partial sequence group is below a load limit and, if so, retain said divisions of said partial sequences of said respective individual partial sequence group and, if not, modify said division of said partial sequences within said respective individual partial sequence group, and/or increase said plurality of partial sequence groups, thereby obtaining at least one of a modified grouping and a modified number of groups;
operate said computerized model of said medical imaging system to check whether said modified grouping or said modified number of groups results in a loading of said at least one component that is below said load limit and, if so, adopt said modified grouping or said modified number of groups as said final division and, if not, again modify said at least one of said grouping and said number of groups until a modified grouping or a modified number of groups, when said operating said computerized model, results in a loading of said at least one component that is below said load limit, as said final grouping or final number of groups; and
emit a designation of said plurality of partial sequences, that conforms to said final grouping or said final number of groups, in electronic form from an output of said computer in a format configured to operate said medical imaging system.

12. A computer for operating a medical imaging system comprising a plurality of components, said computer being programmed to:
receive an electronic designation of a measurement sequence to be executed by said medical imaging system, said measurement sequence comprising a predetermined number of successive partial sequences that each, when executed by said medical imaging system, cause a loading of at least one of said components;
also receive an electronic designation of a measurement period and a division of said measurement period into a measurement interval and a pause interval;
automatically divide said partial sequences into a plurality of partial sequence groups, and designate an initial association of said plurality of partial sequence groups to an equal plurality of said measurement intervals, with a one-to-one relation of said plurality of partial sequence groups to said plurality of measurement intervals;
operate a computerized model of said medical imaging system to initially check whether a loading of at least one of said components with the partial sequences of a respective individual partial sequence group is below a load limit and, if so, retain said divisions of said partial sequences of said respective individual partial sequence group and, if not, modify said division of said partial sequences within said respective individual partial sequence group, and/or increase said plurality of partial sequence groups, thereby obtaining at least one of a modified grouping and a modified number of groups;
operate said computerized model of said medical imaging system to check whether said modified grouping or said modified number of groups results in a loading of said at least one component that is below said load limit and, if so, adopt said modified grouping or said modified number of groups as said final division and, if not, again modify said at least one of said grouping and said number of groups until a modified grouping or a modified number of groups, when said operating said computerized model, results in a loading of said at least one component that is below said load limit, as said final grouping or final number of groups; and
emit a designation of said plurality of partial sequences, that conforms to said final grouping or said final number of groups, in electronic form from an output of said computer in a format configured to operate said medical imaging system.

13. A medical imaging system comprising:
a plurality of system components;
an operating computer;
said computer being configured to receive an electronic designation of a measurement sequence to be executed by said medical imaging system, said measurement sequence comprising a predetermined number of successive partial sequences that each, when executed by said medical imaging system, cause a loading of at least one of said components;

said computer being configured to also receive an electronic designation of a measurement period and a division of said measurement period into a measurement interval and a pause interval;

said computer being configured to automatically divide said partial sequences into a plurality of partial sequence groups, and designate an initial association of said plurality of partial sequence groups to an equal plurality of said measurement intervals, with a one-to-one relation of said plurality of partial sequence groups to said plurality of measurement intervals;

said computer being configured to operate a computerized model of said medical imaging system to initially check whether a loading of at least one of said components with the partial sequences of a respective individual partial sequence group is below a load limit and, if so, retain said divisions of said partial sequences of said respective individual partial sequence group and, if not, modify said division of said partial sequences within said respective individual partial sequence group; and/or increase said plurality of partial sequence groups, thereby obtaining at least one of a modified grouping and a modified number of groups;

said computer being configured to operate said computerized model of said medical imaging system to check whether said modified grouping or said modified number of groups results in a loading of said at least one component that is below said load limit and, if so, adopt said modified grouping or said modified number of groups as said final division and, if not, again modify said at least one of said grouping and said number of groups until a modified grouping or a modified number of groups, when said operating said computerized model, results in a loading of said at least one component that is below said load limit, as said final grouping or final number of groups; and said computer being configured to emit a designation of said plurality of partial sequences, that conforms to said final grouping or said final number of groups, in electronic form from an output of said computer in a format configured to operate said medical imaging system.

\* \* \* \* \*